United States Patent
Novak et al.

(10) Patent No.: US 7,575,720 B2
(45) Date of Patent: Aug. 18, 2009

(54) CAPACITANCE BASED BIOSENSOR

(75) Inventors: James Novak, Austin, TX (US); Prabhu Soundarrajan, Austin, TX (US); Alexei Tikhonski, Cedar Park, TX (US); Zvi Yaniv, Austin, TX (US)

(73) Assignee: Applied Nanotech Holdings, Inc., Austin, TX (US)

( * ) Notice: Subject to any disclaimer, the term of this patent is extended or adjusted under 35 U.S.C. 154(b) by 72 days.

(21) Appl. No.: 11/614,580

(22) Filed: Dec. 21, 2006

(65) Prior Publication Data

US 2007/0151848 A1 Jul. 5, 2007

Related U.S. Application Data

(60) Provisional application No. 60/756,315, filed on Jan. 5, 2006.

(51) Int. Cl.
*G01N 27/00* (2006.01)
(52) U.S. Cl. .................................. 422/82.01
(58) Field of Classification Search ............... 422/82.01
See application file for complete search history.

(56) References Cited

U.S. PATENT DOCUMENTS 6,548,311 B1 * 4/2003 Knoll ......................... 436/524
6,718,819 B2 * 4/2004 Schoess ..................... 73/53.05

FOREIGN PATENT DOCUMENTS

WO   WO 9927367 A1 * 6/1999

OTHER PUBLICATIONS

Kolesar, E. S.; Wiseman, J. M. "Interdigitated Gate Electrode Field Effect Transistor for the Selective Detection of Nitrogen Dioxide and Diiosopropyl Methylphosphonate." Anal. Chem. 1989, 61, pp. 2355-2361.*

Sindi, H. S.; Stevenson A. C.; Lowe, C. R. "A Strategy for Chemical Sensing Based on Frequency Tunable Acoustic Devices." Anal. Cham. 73, 7, pp. 1577-1586.*

Huang, et al., "Prostate-specific antigen immunosensing based on mixed self-assembled monolayers, camel antibodies and colloidal gold enhanced sandwich assays" *Biosensors and Bioelectronics*, vol. 21, Issue 3, pp. 483-490 (Sep. 15, 2005).

Armbruster, D.A., "Prostate-specific antigen: biochemistry, analytical methods, and clinical application" *Clin. Chem.* 39, 181-195 (1993). Published by American Association for Clinical Chemistry, Washington, D.C., U.S.A.

(Continued)

*Primary Examiner*—Walter D Griffin
*Assistant Examiner*—Bobby Ramdhanie
(74) *Attorney, Agent, or Firm*—Fish & Richardson P.C.; Kelly K. Kordzik

(57) ABSTRACT

A method for electronically detecting an electrostatic based biological binding event. This same binding event can be detected optically via complicated experimental setups. A balanced coil system is incorporated into a hand held unit with a plug-in chip. The chip may further be made to act like an array with a different surface molecule for detection of different bio-molecules.

12 Claims, 4 Drawing Sheets

OTHER PUBLICATIONS

Cattini, et al., "Measurement of alpha-fetoprotein, carcinoembryonic antigen and prostate-specific antigen in serum and heparinised plasma by enzyme immunoassay on the fully automated serono SR1 analyzer" *Eur. J. Clin. Chem. Clin. Biochem.* 31, 517-524 (1993). Published in Germany.

Thompson, et al., "Surfaced-Launched Acoustic Wave Sensors: Chemical Sensing and Thin-Film Characterization" pp. 1-196, Published by John Wiley & Sons, New York (1997).

Stenberg, et al., "Quantitative determination of surface Plasmon resonance using radiolabeled proteins," *J. Colloid Interface Sci.* 143, 513-526 (1991). Published in U.S.A.

Pei, et al., "Amplification of antigen-antibody interactions based on biotin labeled protein-streptavidin network complex using Impedance spectroscopy" *Biosensors & Bioelectronics* (2001) 355-361.

Guan, et al., "Impedimetric Biosensors" *Journal of Bioscience and Bioengineering.* (2004) vol. 97, No. 4, 219-226. Published in Japan.

Ouerghi. et al., "Impedimetric Immunosensor using avidin-biotin for antibody immobilization" *Bioelectrochemistry* (2002) 56, 131-133.

Riepl, et al., "Optimization of capictive affinity sensors: drift suppression and signal amplification" *Analytic Chimica Acta* (1999) 392, 77-84.

Mitsky, V., "Capacitive monitoring of protein immobilization and antigen-antibody reactions on monomolecular alkythiol films on gold electrodes" *Biosensors & Bioelectronics* (1997) 12, (9-10) 977-989.

\* cited by examiner

CAPACITANCE BASED BIOSENSOR

This applications claims priority to U.S. provisional patent application Ser. No. 60/756,315.

TECHNICAL FIELD

The present invention relates in general to biological sensors.

BACKGROUND INFORMATION

Biological sensors are used in many areas of human life. The largest problem is one of portability and ease of use. One area of biosensor involves the interaction between an antibody and antigen; however, detection of the binding events when the antibody/antigen pair binds together is difficult due to a lack of electron transfer and the nature of the weak electrostatic forces involved. This drives a need for new transduction methods for the detection of these types of biological reactions.

The term, "biomolecule-binding pairs," means that specific binding will occur between a first member and a second member of a binding pair under defined conditions of ionic strength, temperature, pH and the like. The interaction may occur due to specific electrostatic, hydrophobic, or other interaction of certain residues of the first member with specific residues of the second member to form a stable complex under conditions effective to promote the interaction.

Examples of biomolecule-binding pairs include, protein-protein interactions, protein-nucleic acid interactions, protein-small molecule interactions, nucleic acid-nucleic acid interactions, protein-fatty acid interactions, and protein-lipid interactions. A protein member of a binding pair may be an antigen, antibody, enzyme, hormone, receptor, regulatory protein, membrane protein, glycoprotein, proteoglycan, or a binding fragment, domain, or derivative of any of such proteins. A nucleic acid member of a binding pair may be deoxyribonucleic acid, or ribonucleic acid, binding fragment, domain or derivative of any of such nucleic acids. A member of a binding pair may also be a small molecule, or a substrate, for example.

There are many biosensors that are based on optical techniques. These include surface plasmon resonance (SPR), laser induced fluorescence, and radiolabeling (Huang, et al, "Prostate-specific antigen immunosensing based on mixed self-assembled monolayers, camel antibodies and colloidal gold enhanced sandwich assays," Biosensors and Bioelectronics 21 (2005) 483-490; Armbruster, D. A., 1993, Prostate-specific antigen; biochemistry, analytical methods, and clinical application, Clin. Chem. 39, 181-195; Cattini, R., Cooksey, M., Robinson, D., Brett, G., Bacarese-Hamilton, T., Jolley, N., 1993, Measurement of alpha-fetoprotein, carcinoembryonic antigen and prostate-specific antigen in serum and heparinised plasma by enzyme immunoassay on the fully automated sereno SR1 analyzer, Eur. J. Clin. Chem. Clin. Biochem. 31, 517-524; Thompson, M., Stone, D. C., 1997; Surface-Launched Acoustic Wave Sensors; Chemical Sensing and Thin-Film Characterization, John Wiley & Sons, New York; Stenberg, E., Persson, B., Roos, H., Urbaniczky, C., 1991, Quantitative determination of surface plasmon resonance using radiolabeled proteins, J. Colloid Interface Sci. 143, 513-526).

SPR detects a change in reflected light caused by the bound biological pair on the surface. Usually, SPR is not portable due to sophisticated support electronics that are sensitive to placement and vibration. Fluorescence based methods require extensive modification of the target molecules that allow them to fluoresce light. These methods require that a fluorescent tag is able to be placed onto the target. This also requires intense laser-based excitation of the fluorophor to reach low detection limits. All of the optical techniques require large, complicated electronics to take the measurements. They can be made small enough to be called "bench top," but not small enough to be handheld and portable.

DETAILED DESCRIPTION

Developed is an electrical method for testing biosensors. Electrical measurement of binding biological pairs is difficult. Many biosensors rely on an exchange of electrons during the reaction. This exchange of electrons (oxidation or reduction) of the analyte can be read as a change in resistance or current through the sensor. The problem with most biological reactions is the lack of electron transfer in the reaction. There are no electrons to be measured by conventional conductivity methods. Most biological pairs bond together via weak electrostatic forces. Examples of these pairs are DNA, RNA, and antibody/antigen pairs.

To circumvent the problem of a lack of electron transfer in these antibody/antigen based biological systems, focus must be on the type of bonding. The electrostatic forces that hold these bio-pairs together are usually hydrogen-bonding and electrostatic interactions. Both of these have a characteristic shift in electron density near the bonding site without a transfer of electrons. This transfer of electron density can be thought of as a dielectric shift. The shift in dielectric potential can be measured as a change in capacitance. Advantage of this capacitance shift is taken to create an electrical measurement where it was once not possible. Prior art has shown other measurements of capacitance for bio sensing. Nearly all methods use impedence spectroscopy (Pei, et al., "Amplification of antigen-antibody interactions based on biotin labeled protein-streptavidin network complex using impedance spectroscopy," Biosensors & Bioelectronics (2001) 355-361; Jina-Gou Guan, et al., "Impedimetric Biosensors," Journal of Bioscience and Bioengineering, (2004) Vol. 97, No. 4, 219-226; O. Querghi, et al., "Impedimetric Immunosensor using avidin-biotin for antibody immobilization," Bioelectrochemistry (2002) 56 131-133). Direct capacitance measurements have also been made (M. Riepl, et al. "Optimization of capacitive affinity sensors; drift suppression and signal amplification," Analytic Chimica Acta (1999) 392 77-84; V. Mirsky, "Capacitive monitoring of pritein immobilization and antigen-antibody reactions on monomolecular alkylthiol films on gold electrodes," Biosensors & Bioelectronics (1997) 12 (9-10) 977-989). These previous methods utilize large electronic components. The electrometers, capacitance meters, lock-in amplifiers and analyzers are not portable and it would be impossible to put them into a handheld unit.

Figure 1A:
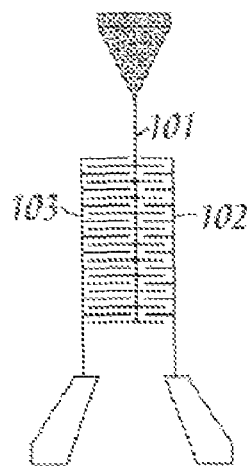
FIG. 1A illustrates a sensor configured in accordance with an embodiment of the present invention.

Referring to FIG. 1A, an embodiment of a biosensor 100 of the present invention utilizes two interdigitated electrodes. A receptor molecule (antibody or antigen) is attached to the electrodes. As an example, an antibody is attached to the surface with a covalent chemical tether. A "Covalent chemical tether" means a linker that is covalently bound to the sensor side of an electrode and to a first member of a biomolecule binding pair. The tether has a terminal functional group useful for such coupling, such as an amide, ester, disulfide, isocyanate or sulfhydryl group. In certain embodiments, the covalent bonding is via a carbon-nitrogen, carbon-sulfur, or a carbon-oxygen bond.

When the corresponding bio-molecule target analyte (antigen) binds to the antibody receptor, there is a change in capacitance between the two electrodes. The change in output signal is measured based on a change in impedance between the electrode pairs. This change in impedance is directly related to the change in capacitance and change in dielectric constant. Both the magnitude of the change (in mV) and the direction of change due to phase shift can be monitored, with each providing separate parts of the information describing the reaction. The work done by Mirsky et al. demonstrates a measurement using a lock-in amplifier to determine phase shift and a direct change in capacitance. The system of an embodiment of the present invention is an indirect measurement in capacitance that may be measured by a voltmeter. This important difference leads to a portable bio-sensing device.

There are several contributions to the change in capacitance. These are all based on individual contributions to the change in dielectric. First, consider the shift in electron density at the bonding site. Due to the relative distribution of charge on each side of the reaction site, this is suspected to be quite small. For example, each antibody/antigen molecule has a large number of positively and negatively charged reaction sites. These usually are balanced and contribute to the overall neutral charge of the molecule. This balance of charge results in a small contribution. A second, significant contribution is based on a charge displacement of the double layer charge on the electrode.

There is a small bias applied between the electrodes. When a drop of solution is placed atop the electrodes, a double-layer of alternating charge aligns at each electrode. The biomolecules have a large volume compared to the ions in the double layer. This size will displace the ions disturbing the double layer at the surface of the electrode. This change in double layer capacitance is measured.

Figure 2:
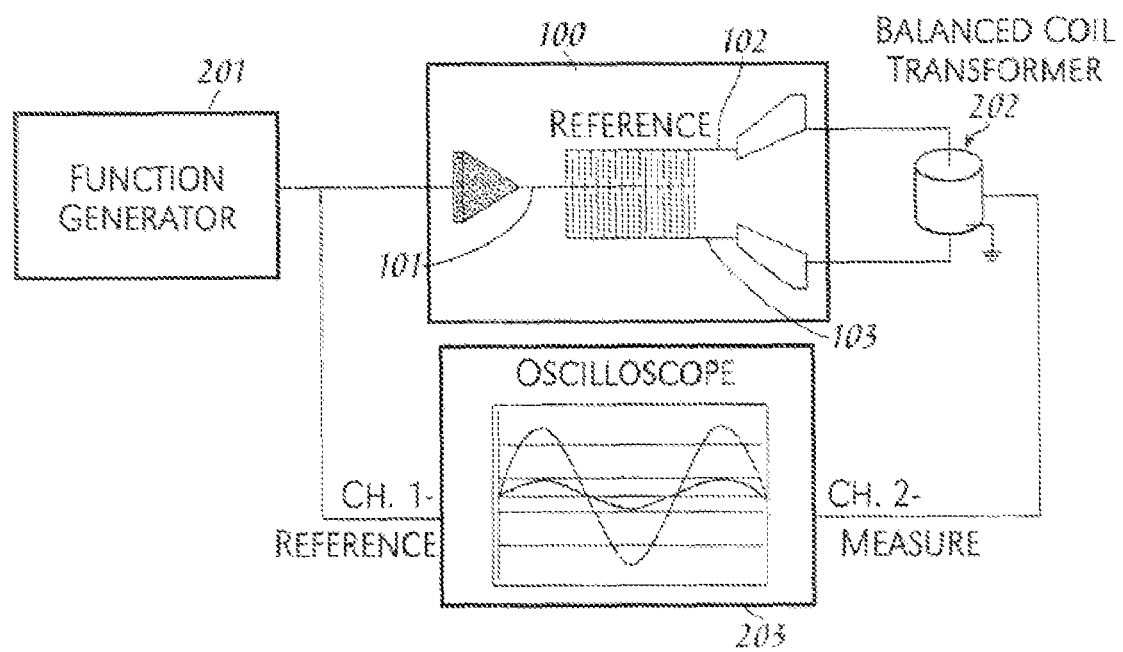
FIG. 2 illustrates a system configured in accordance with an embodiment of the present invention.

An embodiment of the present invention is based upon two pairs of electrodes. There are three electrodes 101-103 in each sensor 100. The center electrode 101 feeds an electrical signal to each adjacent electrode 102, 103. The two outer electrodes 102, 103 have a sensor side 103 and a reference side 102. The reference side 102 is insulated from the fluid by an inert layer. This inert layer is inactive to the biological analyte. In this embodiment the layer is SiO2. In other embodiments the layer could be an electronically insulating organic or inorganic polymer. This inert layer prevents biological molecules from binding to its surface. The sensor side 103 has a surface that is compatible with the binding of a biological layer. In one embodiment, the surface is gold and will accept a thiol-based tether to secure the antibody. As shown in FIG. 2, the outputs of the sensor 103 and reference 102 electrodes are fed into a balanced transformer coil 202. This allows for amplification of the difference in output between the reference 102 and sensor 103 side. The inputs are balanced so the output from the coil 202 is "zero" before the sensor activates.

In addition to detection of binding between binding pairs, the present biosensor is useful for identifying agonists or antagonists of such binding by observing a change in impedance measurements in the presence of the agonist or antagonist as compared to impedance measurements in the absence of such agents.

Figure 1C:
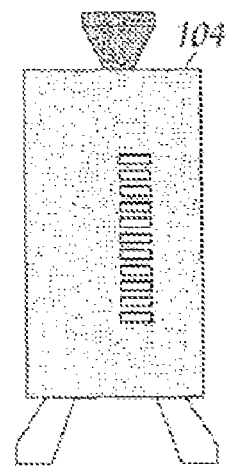
FIG. 1C illustrates an insulator layer on a sensor in accordance with an embodiment of the present invention.
Figure 1B:
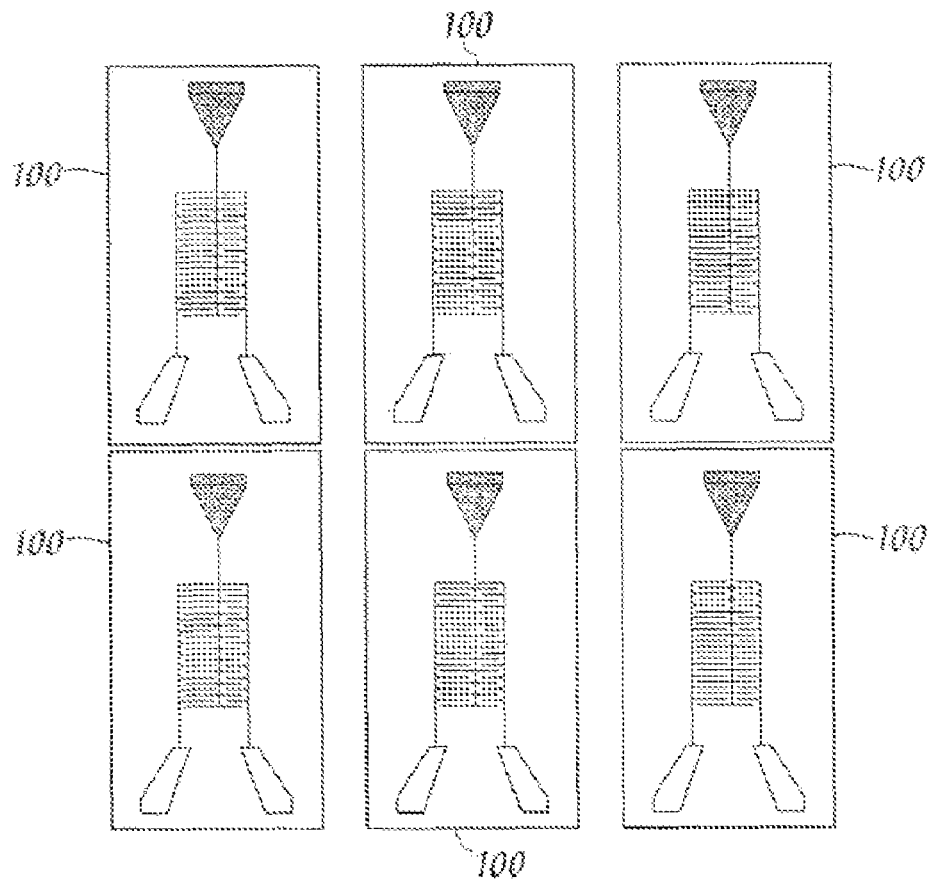
FIG. 1B illustrates a sensor array configured in accordance with an embodiment of the present invention.

An interdigitated array of gold electrodes 101-103 may be patterned onto a glass substrate using standard photolithography techniques. The gold electrodes allow for each surface modification by the analyte receptor. Each substrate may be comprised of two pairs of interdigitated electrodes sharing a common center feed. One pair will be considered a "sensor side" and one pair will be considered a "reference side". The electrodes may be connected via feed lines that are non-parallel to reduce background capacitance. These feed lines may connect to trapezoidal shaped contact pads. Their shape may also be engineered to prevent background capacitance. As shown in FIG. 1C, an insulating oxide layer 104 prevents derivitization of the reference side 102 of the electrodes. The insulating oxide layer is configured so that it covers completely the reference side of the sensor electrodes. The insulating oxide layer has openings (vias) that allow derivatization of the sensor side of the electrodes. As shown in FIG. 1B, there may be six sets (or any number) of electrodes on each substrate."

The substrate should not be conductive or have an underlying conductive layer. An underlying conductive layer (for example, a Si underlayer on a thermal $SiO_2$ wafer) will have a larger capacitance with the surface electrodes than can be measured due to the bio-molecule reaction. This parasitic capacitance may swap out the measurable signal. An example of an insulating substrate would be polymer, plastic, glass, alumina or sapphire.

The electrodes 101-103 may be patterned on the substrates using standard photolithography techniques. First, photo-resist (Shipley S1813, Rohm & Haas), may be deposited by spin-coating onto a clean glass substrate and then soft-baked in an oven at 90° C. for 45 minutes. The photo-resist layer may then be patterned by exposure to UV light (Cannon PLA-501F Mask Aligner) through an interdigitated electrode layer mask. The pattern may be developed using an aqueous solution of AZ 400K Developer (3:1% Vol, AZ Electronics Materials Corp.) The developed resist layer may be cleaned using a Reactive Ion Etch (Ar-ion etch, 102 Watts, 98 mtorr, Model RF5S, RF Power Products) prior to thin-film deposition. The gold electrodes may be deposited using an electron-beam evaporator (PlasmaTron P-30). 100 Å of chrome may be used as an adhesion layer followed by 500 Å of gold. The electrode pattern may then be developed by immersion in an acetone bath. Once lift-off is complete, the substrates may be rinsed with acetone followed by isopropanol, and finally dried under a $N_2$ stream.

The substrates may then be patterned using the same methods as above using the insulating layer maskset. After resist patterning and development, 750 Å of $SiO_2$ may be deposited. This layer may be developed using the same lift-off procedure described above.

As described, the interdigitated electrode pattern on the substrates may consist of three electrodes 101-103 which share the center electrode and comprise two pairs. Impedance between each pair of electrodes is measured. The direct capacitance of each electrode system is not measured, but rather looking at a change in impedance balance between the two pairs of electrodes. The change in impedance is directly related to the change in capacitance between the electrodes.

There may be a measurable change in capacitance based on the binding of biological molecules between the electrodes.

A schematic of the connections is shown in FIG. 2. A Wavetek Function generator 201 may deliver a 500 kHz, 3 Vpp sine wave input signal to the center electrode 101. The resulting output signal is delivered through each secondary electrode 102-103 for the sensor and reference sides, respectively. The sensor side 103 has been derivatized as described above. The reference side 102 may be coated with an insulating oxide as described above. The output from each electrode is then fed into a balanced transformer coil 202. When the capacitance and resulting impedance for each side of the electrode is equal, the resulting output from the coil transformer 202 is zero. The coil output may be then sent to an oscilloscope 203 (Tektronix 2467 350 MHz), which allows measurement of the output voltage and any phase shift that may occur.

The capacitance of the dry electrodes may be balanced empirically by extending the length of the reference side of the electrodes. The length may be 1.5 times that of the sensor side. This difference may be an approximation based on the difference in dielectric constants of the insulating oxide layer and the electrode/biological/fluid layer present on the sensor side. This approximation results in a background signal that is 0.2% (7 mV output with 3V input) of the input when measured on the oscilloscope 203.

Exemplary biological derivitizations were carried out. Multiple substrates were prepared. Each substrate had 6 sets of electrodes as shown in FIG. 1B. Electrical measurements were taken after each step of the reaction. First, an amine-terminated thiol was attached to the gold surface. Second, biotin-NHS was attached to the amine group via an amide linkage. Streptavidin (SA) was then attached to the biotin. This SA was fluorescently labeled to verify binding. Successive bindings of anti-streptavidin were added.

Figure 3:
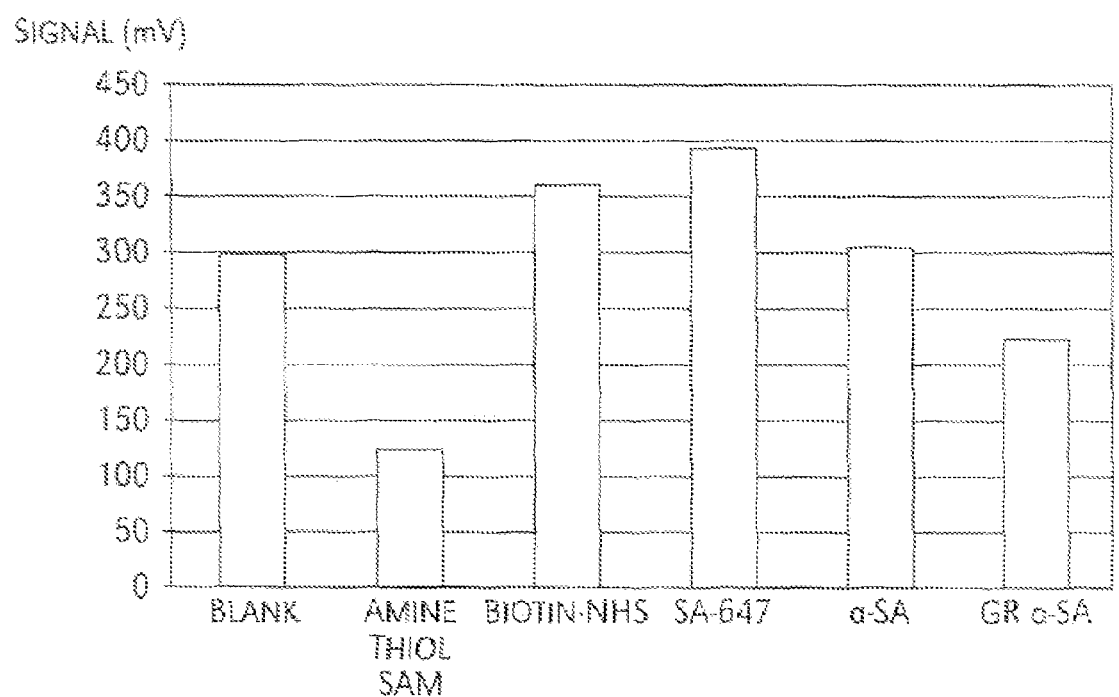
FIG. 3 illustrates a graph of sensed biological substances.

FIG. 3 shows output voltages from the oscilloscope 203 for each step of derivitization. It is clear that a large change in signal is present after each successive derivitization. This shows that there is a measurable change in capacitance due to the binding of each bio molecule. This simple change in voltage may be measured using a hand-held, portable device. It may also be designed into an integrated "package" with a plug-in bio-chip.

In addition to the change in output voltage, phase-shift may be monitored. This phase shift may be important for determining a difference between two molecules that show the same capacitance difference. The phase shift may be able to identify an increase or decrease in capacitance depending on direction. The phase shift may determine the difference between a reacted bio-molecule pair and a physisorbed non-reacted molecule. The phase shift may determine a change in dielectric constant, dipole moment and/or polarizability when combined with a magnitude of change.

Figure 4:
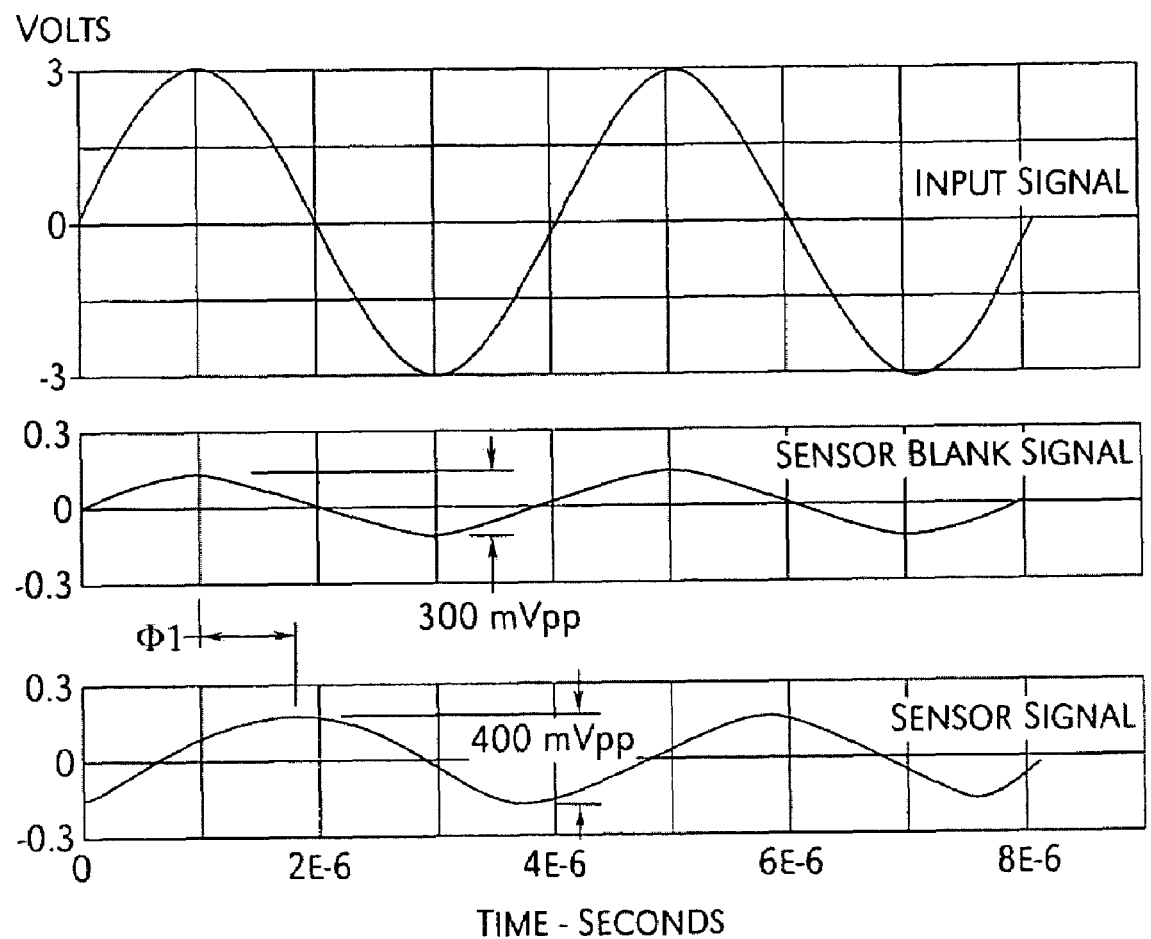
FIG. 4 illustrates an exemplary output from the oscilloscope illustrating measurements of the output signal from the transformer coil.

FIG. 4 illustrates a diagram of how phase shift may enhance information gathered from the sensor. It shows the output signal from an oscilloscope. The vertical axis depicts the magnitude of the signal and the horizontal axis is the sine wave as a function of time. Three traces are offset and scaled for clarity. The upper trace is the input sine wave (3 Vpp) to the center electrode. The middle trace is the resulting output from the transformer. It has the same phase as the input signal but different (much smaller) magnitude at 300 mVpp. The lower trace is the resulting output after the sensor responds. The magnitude has changed to 400 mVpp and the phase has shifted by Φ1. The direction of the phase may tell us if there is an increase or decrease in capacitance relative to the initial input. For example, the same curve may be read as a phase shift, Φ2, in the opposite direction.

The invention claimed is:

1. A sensor comprising:
a first pair of interdigitated electrodes comprising an active node;
a second pair of interdigitated electrodes comprising a reference node;
a center electrode coupled to the first and second pairs of interdigitated electrodes;
a sine wave generator delivering a sine wave input signal to the center electrode;
a balanced transformer coil receiving outputs from each of the active and reference nodes; and
a device for measuring an output of the balanced transformer coil.

2. The sensor as recited in claim 1, wherein the device is an oscilloscope.

3. The sensor as recited in claim 1, wherein the active node is exposed to a biological substance.

4. The sensor as recited in claim 3, wherein the reference node is insulated from exposure to the biological substance.

5. The sensor as recited in claim 4, wherein the reference node is coated with an insulating oxide.

6. The sensor as recited in claim 1, wherein the device measures a voltage level of the output from the balanced transformer coil.

7. The sensor as recited in claim 1, wherein the device measures a phase shift of the output from the balanced transformer coil.

8. The sensor as recited in claim 1, wherein an analyte receptor is disposed on at least one of the first pair of interdigitated electrodes.

9. A sensor comprising:
a substrate;
a first capacitor formed on the substrate and defining a first gap in which an analyte receptor is secured to the first capacitor;
a second capacitor formed on the substrate and defining a second gap, wherein the first capacitor and the second capacitor share a common node;
an input terminal formed on the substrate and electrically connected to the common node;
a first output terminal formed on the substrate and electrically connected to the first capacitor; and
a second output terminal formed on the substrate and electrically connected to the second capacitor, wherein the first capacitor and the second capacitor are each connected in series between the first output terminal and the second output terminal through a balanced coil transformer.

10. The sensor as recited in claim 9, wherein the first capacitor comprises two interdigitated electrodes, one of which is connected to the first terminal, and one or which is connected to the common node.

11. The sensor as recited in claim 9, comprising an insulating layer formed in the second gap but not in at least part of the first gap, wherein the insulating layer is capable of preventing a fluid from flowing into the second gap.

12. The sensor of claim 9, comprising:
a wave-form generator electrically connected to the input terminal, wherein the balanced coil transformer comprises:
a primary winding electrically connected in series between the first output terminal and the second output terminal; and
a secondary winding electrically connected to a voltmeter a phase-difference sensor, or both.

\* \* \* \* \*